United States Patent
Kleiner

(10) Patent No.: US 9,089,412 B2
(45) Date of Patent: Jul. 28, 2015

(54) MULTILAYER BIOABSORBABLE SCAFFOLDS AND METHODS OF FABRICATING

(71) Applicant: Abbott Cardiovascular Systems Inc., Santa Clara, CA (US)

(72) Inventor: Lothar W. Kleiner, Los Altos, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 40 days.

(21) Appl. No.: 13/855,638

(22) Filed: Apr. 2, 2013

(65) Prior Publication Data

US 2013/0261736 A1     Oct. 3, 2013

Related U.S. Application Data

(60) Provisional application No. 61/619,231, filed on Apr. 2, 2012.

(51) Int. Cl.

| | | |
|---|---|---|
| *B32B 1/08* | (2006.01) |
| *A61F 2/06* | (2013.01) |
| *B29C 47/06* | (2006.01) |
| *B32B 27/00* | (2006.01) |
| *A61L 31/06* | (2006.01) |
| *A61L 31/14* | (2006.01) |
| *C08L 67/04* | (2006.01) |
| *C08L 71/02* | (2006.01) |
| *B29C 47/14* | (2006.01) |
| *B29C 47/56* | (2006.01) |
| *B29C 47/70* | (2006.01) |

(Continued)

(52) U.S. Cl.
CPC . *A61F 2/06* (2013.01); *A61L 31/06* (2013.01); *A61L 31/148* (2013.01); *B29C 47/06* (2013.01); *B29C 47/145* (2013.01); *B29C 47/56* (2013.01); *B29C 47/707* (2013.01); *B32B 27/00* (2013.01); *B32B 27/36* (2013.01); *C08L 67/04* (2013.01); *C08L 71/02* (2013.01); *A61F 2/82* (2013.01); *A61F 2002/91566* (2013.01); *A61F 2210/0004* (2013.01); *A61F 2210/0076* (2013.01); *Y10T 428/1393* (2015.01)

(58) Field of Classification Search
CPC ....... A61F 2/82; A61F 2002/825; A61F 2/86; A61F 2/90; B32B 1/08; Y10T 428/139; Y10T 428/1393
USPC ........... 623/1.11, 1.13, 1.15, 1.38, 1.42–1.49; 428/36.9, 36.91
See application file for complete search history.

(56) References Cited

U.S. PATENT DOCUMENTS 7,244,441 B2 *  7/2007  Schreiner ...................... 424/422
7,632,307 B2 * 12/2009  Pacetti et al. ................ 623/1.44

(Continued)

OTHER PUBLICATIONS

Angioplasty Summit Abstracts/Oral, The Am. J. of Cardiology, Apr. 23-26, 2013, p. 23B.

(Continued)

*Primary Examiner* — Walter B Aughenbaugh
(74) *Attorney, Agent, or Firm* — Squire Patton Boggs (US) LLP

(57) ABSTRACT

A bioabsorbable scaffold composed of a multilayer structure of alternating layers of different polymers is disclosed. The multilayer structure can have 20 to 1000 layers and the individual thickness of the layers can be 0.2 to 5 microns. A method of making the scaffold including a layer multiplying extrusion process is disclosed.

7 Claims, 5 Drawing Sheets

(51) Int. Cl.
*B32B 27/36* (2006.01)
*A61F 2/82* (2013.01)
*A61F 2/915* (2013.01)

(56) References Cited

U.S. PATENT DOCUMENTS

| | | |
|---|---|---|
| 2007/0283552 A1 | 12/2007 | Gale et al. |
| 2008/0275537 A1 | 11/2008 | Limon |
| 2009/0146348 A1 | 6/2009 | Huang et al. |
| 2010/0004735 A1 | 1/2010 | Yang et al. |
| 2011/0190871 A1 | 8/2011 | Trollsas et al. |
| 2011/0190872 A1 | 8/2011 | Anukhin et al. |

OTHER PUBLICATIONS

Bosiers et al., "Coronary and endovascular applications of the Absorb™ bioresorbable vascular scaffold", Interv. Cardiol. 4(6), pp. 621-631 (2012).

Liu et al., "Interphase materials by forced assembly of glassy polymers", Macromolecules 37, pp. 6972-6979 (2004).

Miller "Abbott's Bioresorbable Stent Shows Durable Results in ABSORB Trial", The Gray Sheet, pp. 17-18, Mar. 2003.

Van Vlack "Elements of materials science and engineering", Addison-Wesley sixth Ed. 4 pgs. (1989).

\* cited by examiner

MULTILAYER BIOABSORBABLE SCAFFOLDS AND METHODS OF FABRICATING

This application claims the benefit of U.S. application Ser. No. 61/619,231 filed on Apr. 2, 2012, which is incorporated by reference herein.

BACKGROUND OF THE INVENTION

1. Field of the Invention

This invention relates polymeric medical devices, in particular, bioabsorbable stent scaffolds composed of a multilayer polymer material.

2. Description of the State of the Art

This invention relates to radially expandable endoprosthesis, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a balloon catheter assembly so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the scaffold as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Crimping and expansion are the most significant forces imposed on the scaffold during use. Crimping and expansion cause deformation of the scaffold material beyond its elastic region, thus imposing the greatest potential for damage to the scaffold.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from a material that erodes, resorbs or disintegrates through exposure to conditions within the body. Stents fabricated from biodegradable, bioabsorbable, bioresorbable, and/or bioerodable materials such as bioabsorbable polymers can be designed to completely resorb only after the clinical need for them has ended.

The development of a bioresorbable stent or scaffold could obviate the permanent metal implant in vessel, allow late expansive luminal and vessel remodeling, and leave only healed native vessel tissue after the full absorption or resorption of the scaffold. A fully bioabsorbable stent can reduce or eliminate the risk of potential long-term complications and of late thrombosis, facilitate non-invasive diagnostic MRI/CT imaging, allow restoration of normal vasomotion, provide the potential for plaque regression.

However, there are several challenges making a fully bioabsorbable polymeric stent. These include making a stent with sufficient radial strength, stiffness, toughness or resistance to fracture, and a suitable degradation rate.

INCORPORATION BY REFERENCE

All publications, patents, and patent applications mentioned in this specification are herein incorporated by reference to the same extent as if each individual publication or patent application was specifically and individually indicated to be incorporated by reference, and as if each said individual publication, patent, or patent application was fully set forth, including any figures, herein.

SUMMARY OF THE INVENTION

Various embodiments of the present invention include a stent comprising a bioresorbable scaffolding including a plurality of structural elements, the structural elements made of a multilayer structure composed of alternating bioresorbable polymer layers, wherein adjacent layers of the polymer layers are made of different polymer materials, wherein a thickness of the layers is between about 0.2 and 5 microns.

Additional embodiments of the present invention include a method of making a radially expandable scaffold comprising: conveying a first polymer melt of a first bioresorbable polymer material and a second polymer melt of a second bioresorbable polymer material through n die elements to form a multilayer polymer melt having $2^{(n+1)}$ layers, wherein n is greater than 3, wherein the multilayer polymer melt is composed of alternating layers of the first polymer melt and the second polymer melt; and forming a tubular construct from the multilayer polymer melt composed of alternating layers of the first bioresorbable material; and forming a radially expandable scaffold from the tubular construct made of structural elements composed of a multilayer structure of alternating layers comprising the first polymer material and the second polymer material.

Further embodiments of the present invention include a method of making a radially expandable scaffold comprising: conveying at least two polymer melts each composed of a different polymer material from extruders to form a structure having layers of the at least two polymer melts, conveying the layered structure through n die elements to form a multilayer structure composed of alternating layers of the different polymer materials, wherein as the polymer melts pass through a die element of the n die elements a new multilayer structure is formed having twice the number of layers; conveying the multilayer structure through a final die element to form a tubular construct composed of alternating layers of the different polymer materials; and forming a scaffold from the tubular construct.

DETAILED DESCRIPTION OF THE INVENTION

Various embodiments of the present invention include scaffolds having a multilayer polymer structure made from multilayer polymer materials. Embodiments further include methods of making such scaffolds that include fabricating a multilayer polymer melt using a layer multiplying technique and making a polymer tube from the multilayer melt.

The methods described herein are generally applicable to any amorphous or semi-crystalline polymeric implantable medical device, especially those that have load bearing portions when in use or have portions that undergo deformation during use. In particular, the methods can be applied to tubular implantable medical devices such as self-expandable stents, balloon-expandable stents, and stent-grafts.

Figure 1:
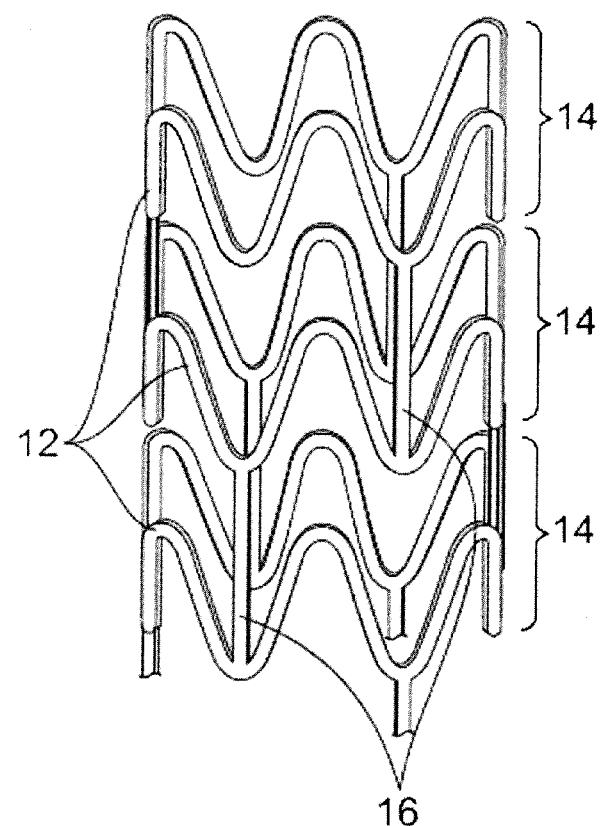
FIG. 1 depicts a stent.

A stent may include a pattern or network of interconnecting structural elements or struts. An exemplary structure of a stent is shown in FIG. 1. FIG. 1 depicts a stent 10 which is made up of struts 12 with gaps between the struts. Stent 10 has interconnected cylindrical rings 14 connected by linking struts or links 16. The outer surface of the struts is the abluminal surface and the inner surface of the struts is the luminal surface. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

A stent of the present invention can be made partially or completely from a biodegradable, bioresorbable, and bioabsorbable polymer or polymers. The stent can also be made in part of a biostable polymer. A polymer for use in fabricating a stent can be biostable, bioresorbable, bioabsorbable, biodegradable, or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

Bioabsorbable stents can be useful for treatment of various types of bodily lumens including the coronary artery, superficial femoral artery, neural vessels, and the sinuses. In general, these treatments require the stent to provide mechanical support to the vessel for a period of time and then desirably to absorb away and disappear from the implant site. The important properties of a bioabsorbable stent or scaffolding include mechanical and degradation properties. The mechanical requirements include high radial strength, high radial stiffness, and high fracture toughness. The degradation properties include the repeatable absorption profile, for example, the change in molecular weight, radial strength, and mass with time.

A scaffold made from a bioabsorbable polymer may be designed to maintain its radial strength once implanted to provide mechanical support to the vessel and maintain patency of the lumen. The radial strength must be sufficiently high initially to support the lumen at an expanded or desired diameter. The period of time that the scaffolding is required or desired to maintain patency depends on the type of treatment, for coronary treatment it is about 3 months. After this time period, the vessel is healed sufficiently to maintain an expanded diameter without support. Therefore, after this time period, the scaffolding may start to lose radial strength due to molecular weight degradation. As the scaffolding degrades further, it starts to lose mechanical integrity and then experiences mass loss and eventually absorbs away completely or there are negligible traces left behind.

Ideally, it is desired that once the stent support is no longer needed by the lumen, the bioabsorbable scaffold is absorbed as fast as possible while also meeting all basic safety requirements during its degradation period. Such safety requirements can include a gradual disintegration and resorpton that does not allow release of fragments that could cause adverse events such as thrombosis. By the time disintegration occurs, the tissue has totally encapsulated the stent, so no fragments are released. In this way, the stent scaffolding enables the vessel healing as well as enabling the advantages mentioned herein of a bioresorbable scaffolding to the greatest extent. It is desirable for a bioabsorbable stent to have an absorption time of about 18 to 26 months for coronary vascular application, of about eighteen months (e.g., 16-20 months) for a peripheral application (e.g., superficial femoral artery (SFA)), 18-24 months for neural applications, and less than a year for nasal applications.

The mechanical requirements of bioabsorbable scaffolding include high radial strength, high stiffness or high modulus, and high fracture toughness. With respect to radial strength and stiffness, a stent should have sufficient radial strength to withstand structural loads, namely radial compressive forces, imposed on the stent so that the stent can supports the walls of a vessel at a selected diameter for a desired time period. A polymeric stent with adequate radial strength and/or stiffness enables the stent to maintain a lumen at a desired diameter for a sufficient period of time after implantation into a vessel.

In addition, the stent should possess sufficient toughness or resistance to fracture to allow for crimping, expansion, and cyclic loading without fracture or cracking that would compromise the function of the stent. The toughness or resistance to fracture can be characterized for a material by the elongation at break and for a stent by the number and degree of cracks in a scaffold after use, (especially in the rings), such as after crimping or deployment. These aspects of the use of the stent involve deformation of various hinge portions of the structural elements of the scaffolding.

Semicrystalline polymers that are stiff or rigid under biological conditions or conditions within a human body have been shown to be promising for use as a scaffold material. Specifically, polymers that have a glass transition temperature (Tg) sufficiently above human body temperature which is approximately 37° C., should be stiff or rigid upon implantation. Poly(L-lactide) (PLLA) is attractive as a stent material due to its relatively high strength and a rigidity at human body temperature, about 37° C. As shown in Table 1, PLLA has high strength and tensile modulus compared to other biodegradable polymers. Since it has a glass transition temperature well above human body temperature, it remains stiff and rigid at human body temperature. This property facilitates the ability of a PLLA stent scaffolding to a maintain a lumen at or near a deployed diameter without significant recoil (e.g., less than 10%).

Semicrystalline polymers with Tg's above human body temperature such as PLLA may exhibit a brittle fracture mechanism in which there is little or no plastic deformation prior to failure, as shown by the low elongation to failure. This polymer, as a result of its chemical structure, is inherently brittle, especially after physical aging. Fracture occurs through a crazing mechanism.

However, it has been demonstrated that the fracture toughness as well as the radial strength is dramatically improved through various processing methods (e.g., radial expansion and suitable choice of associated processing parameters) as shown in US-2009-0146348. Specifically, PLLA scaffolds exhibit significant enhancement through biaxial orientation created by an expansion process which results in rapid strain-induced crystallization. However, there is a still an incentive to employ other methods solely or in combination to make bioresorbable polymer scaffolds with high strength and high fracture resistance.

The present invention includes the use of a layer multiplying co-extrusion process to fabricate multilayer scaffolds which increase the fracture toughness of a bioresorbable scaffold. A layer multiplying extrusion process is described in, for example, R. Y. F. Liu, et al., Macromolecules, 37, 6972-6979 (2004). The increase in fracture toughness is achieved in at least two ways. First, the multilayer morphology with very thin layers increases fracture toughness by arresting crack propagation. Second, fracture toughness is increased through appropriate selection of material for different polymer layers. The multilayer structure can include layers of polymers of high strength, stiff polymers alternating with layers that are more flexible and less susceptible to fracture. The combination and arrangement of rigid and flexible polymer materials provides fracture toughness while maintaining strength and stiffness of the scaffold. Additionally, the multilayer structure may be less prone to fracture since a thinner layer is less susceptible to fracture than a corresponding thicker layer, e.g., a scaffold that is composed of a single layer of rigid polymer.

In general, the fracture toughness of a brittle polymer material can be increased by forming phase separated morphology or a composite of the brittle polymer with a polymer having a high fracture toughness under physiological conditions. Physiological conditions refers to human body temperature or about 37 deg C and exposure to bodily fluids. The brittle polymer and high fracture toughness polymer may be miscible or partially miscible or at least interfacially compatible. A "composite" refers generally to a material in which two or more distinct, structurally complementary substances combine to produce structural or functional properties not present in any individual components.

In the present invention, the structural elements of the scaffold are composed of alternating layers of brittle or low fracture toughness polymer and high fracture toughness polymer. It is believed that fracture toughness of the composite is increased or enhanced by the properties of high fracture roughness polymer. Also, fracture toughness of the composite is increased due to interruption of crack propagation in a direction transverse to the layers. It is believed that the thinner the layers, the more effective the increase in fracture toughness since the fracture is interrupted over a shorter length scale.

Embodiments of the present invention include conveying at least two polymer melts, each composed of a polymer material, through n die elements to form a multilayer melt material. The polymers of the at least two melts are immiscible or partially miscible so that that a phase separated morphology is stable even in a melt state. Each polymer melt is composed of a polymer material, for example, a bioresorbable polymer material. The polymer melts can be conveyed from separate extruders to form a layered material with adjacent layer joined at their surfaces prior to passing through any of the die elements. As the polymer melts pass through a die element, the number of layers is multiplied by 2. The layers correspond to the polymer material of polymer melts.

A tubular construct having a multilayer morphology is formed from the multilayer polymer melt with appropriate die design disclosed herein. A scaffold including a plurality of structural elements may then be formed from the tubular construct. Optionally, intervening processing steps can be performed on the multilayer tubular construct prior to forming the scaffold, such as annealing, deformation (radial expansion and/or axial elongation), or both.

There may be localized entanglement of the interfacially compatible immiscible or partially immiscible polymers of the adjacent layers at the interface of the layers. The localized entanglement provides adhesion or bonding between the layers. This bonding facilitates or ensures good energy transfer between interfaces of the phases. It is important that there be sufficient bonding or adhesion between the phases. It is believed that the bonding helps the layered structure remain stable and provides uniform energy transfer to interrupt fracture interruption, and thus improved fracture resistance.

In an exemplary embodiment, a first polymer melt of a first polymer material and a second polymer melt of a second polymer material are conveyed through n die elements to form a multilayer polymer melt having $2^{(n+1)}$ layers. In some embodiments, n is greater than 3 or greater than 4.

Figure 2:
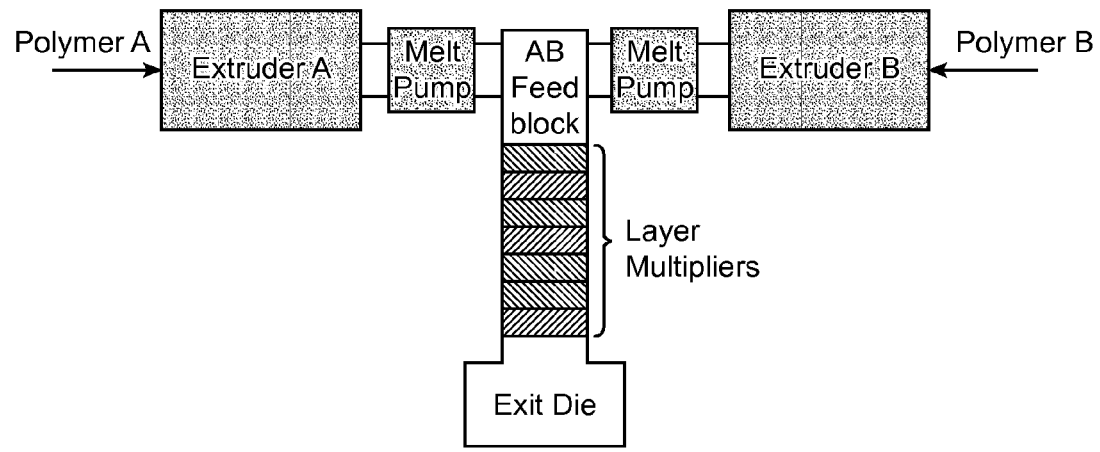
FIG. 2 depicts a schematic of a system for forming a multilayer melt from two different polymer melts.

FIG. 2 depicts a schematic of a system for forming a multilayer melt from two different polymers, polymer A and polymer B. A polymer melt of polymer A is fed from extruder A by a melt pump and a polymer melt of polymer B is fed from extruder B by a melt pump into a feed block. A two layer structure is formed in the feed block which is passed through layer multipliers which are a series of die elements. The multilayer melt that is formed from the layer multipliers is passed through an exit die to form a multilayer polymer construct.

In general, N polymer melts (Nm), that may come from Nm extruders, may be joined to form an Nm layer structure which is passed through n die elements of a layer multiplier assembly to form a multilayer polymer melt having $Nm \times 2^n$ layers. The Nm melts can be the same material, all different materials, or include different subsets of materials, with each subset made of the same material. For example, for Nm=3, all three melts may be different, e.g., polymers A, B, and C, and the multilayer structure may be ABCABCABC, etc. In another example for Nm=3, two polymer melts may be the same (e.g., polymer A) and different from the third (e.g. polymer B) and the multilayer structure may be ABAABAABA, etc.

A desired geometry of the multilayer polymer construct can be formed through selection of an exit die of an appropriate geometry. For example, a die with a circular annulus can be used to form a tube with a multilayer morphology. The system in FIG. 2 can be modified to accommodate three or more polymers. In such modifications, the number of polymers used is equal to the number of extruders.

The thickness of the multilayer structure depends on the thickness of each layer and number of layers. When 2 die elements of the layer multipliers are chosen, there will be 8 layers and if each layer is 19 microns thick, the total thickness of the multilayer melt is 150 microns. If 8 die elements are chosen, then 512 layers are created and if each layer is 0.29 microns thick, the total thickness of the multilayer melt is 150 microns.

Figure 3:
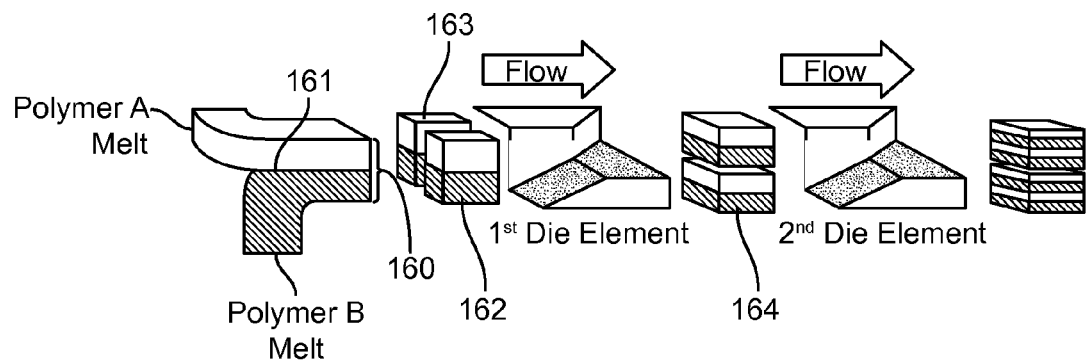
FIG. 3 depicts a schematic illustration of layer-multiplying coextrusion for forming a multilayer polymer melt from a polymer A melt and a polymer B melt.

FIG. 3 depicts a schematic illustration of layer-multiplying coextrusion process for forming a multilayer polymer melt from a polymer A melt and a polymer B melt. FIG. 3 illustrates how two die elements multiply the number of layers from 2 to 8. A layer in the form of a sheet of polymer A melt and a layer in the form a sheet of polymer B melt are joined to form a two layer melt 160 with an interface 161. The two layer melt is split transverse to the interface along the direction of flow, as shown by the arrows. As shown, layers 162 and 163 pass through a first die element which reorients and rejoins 162 and 163 to form an alternating four layer melt 164. The four layer melt passes through a second die element which splits the four layer melt 164 and reorients and rejoins it to form an alternating eight layer melt. Thus, an assembly of n die elements receiving polymer melts from two extruders produces a multilayer polymer melt having $2^{(n+1)}$ layers in the form of a sheet.

Figure 4A:
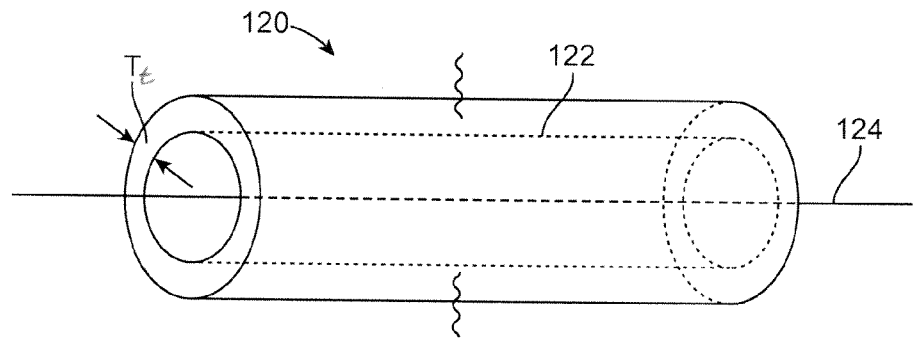
FIG. 4A depicts a perspective view of a tube.
Figure 4B:
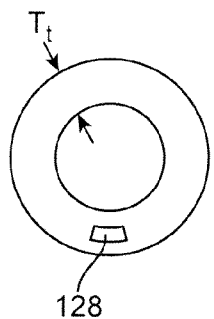
FIG. 4B depicts a radial cross-section of the tube in FIG. 4A.
Figure 4C:
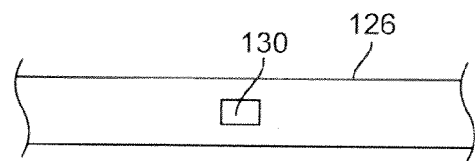
FIG. 4C depicts a cross-section through the wall of the tube in FIG. 4A parallel to the axis of the tube.

FIG. 4A depicts a perspective view of a tube 120 with an outer surface 122 and cylindrical axis 124. Tube 120 has a thickness $T_t$. FIG. 4B depicts a radial cross-section of tube 120 and FIG. 4C depicts a cross-section 126 through the wall of tube 120 parallel to axis 124 of tube 120.

Figure 5A:
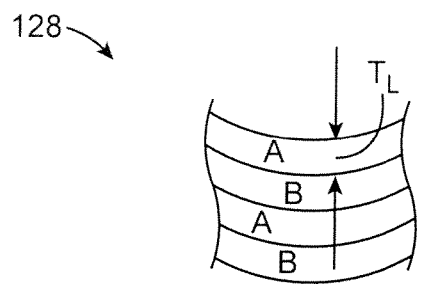
FIG. 5A shows an expanded view of a section of a multilayer structure having alternating layers of polymer A and B.
Figure 5B:
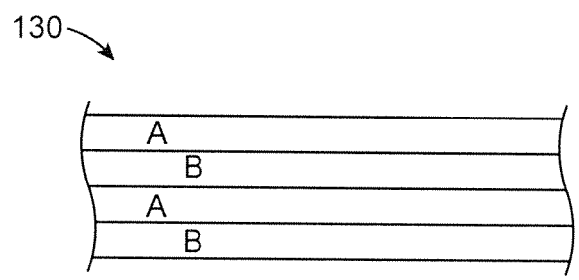
FIG. 5B shows an expanded view of a section from a scaffold side wall showing the alternating layers of polymer A and polymer B.

FIG. 5A shows an expanded view of a section 128 showing the multilayer structure having alternating layers of polymer A and B. FIG. 5B shows an expanded view of a section 130 from section 126 of the wall also showing the alternating layers of polymer A and polymer B. Layers A, for example, have a thickness $T_L$. In FIGS. 5A-B, the layers are shown to be concentric around the cylindrical axis 124 of tube 120 such that layers of polymer A and B alternate between the inner and outer surfaces of the tube. In further embodiments, the orientation of the layers can deviate from the concentric structure.

Embodiments of the present invention include a radially expandable scaffold composed of a plurality of structural elements. Such a scaffold is formed from a polymer construct fabricated using the layer multiplying method described above. In such embodiments, a scaffold in fabricated by cutting a pattern into the multilayer structure to form pattern of structural elements. The structural elements are made completely or partially of a multilayer material, composite, or architecture composed of a plurality of polymer layers. A "layer" refers to a single thickness of a material forming a segment of a material. The multilayer material includes alternating layers made of different polymer materials. Thus, adjacent layers of the alternating polymer layers are made of different polymer materials.

In some embodiments, the multilayer morphology can extend between the luminal and abluminal surface of a scaffold. In other embodiments, the scaffold can include additional layers not formed by the layer multiplying process. The additional layer(s) may be a different polymer, different thickness, include additives such as a drug not included in the multilayer structure. In such embodiments, one or more additional layers may be formed on the multilayer tube of the layer multiplying extrusion process. The layer may be formed through a coextrusion process, spraying, or dipping. In a coextrusion process, a polymer layer may be coextruded on the inside or outside surface the multilayer structure. Alternatively, a coating material including a polymer and a solvent solution may be applied by spraying followed by removal of the solvent to form the polymer layer on the inside surface, outside surface, or both of the multilayer tube. A polymer layer may also be formed using the polymer solution using dipping on such surface(s).

Additionally or alternatively, a polymer coating can be applied on at least a part or on the entire surface of the scaffold formed from a multilayer tube. The polymer coating may include a drug. The drug may include an antiproliferative, anti-inflammatory, or both such as everolimus, rapamycin or any of its derivatives, zotarolimus, and novolimus.

Figure 6:
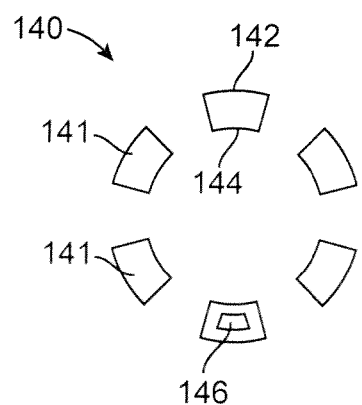
FIG. 6 depicts a radial cross-section of a scaffold cut from a multilayer tubular construct.

FIG. 6 depicts a radial cross-section of a scaffold 140 cut from a multilayer tubular construct cut, such as tube 120. Scaffold 140 has structural elements 141 which have an abluminal surface 142 and a luminal surface 144. An expanded view of a section 146 of structural element 141 is as shown in FIG. 5A.

Figure 7:
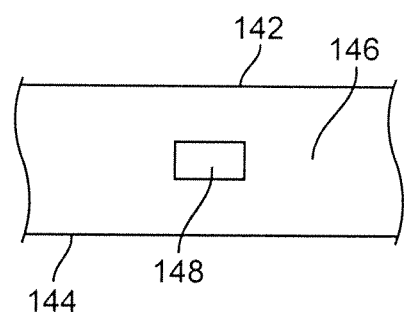
FIG. 7 depicts a portion of a structural element with a view facing a side wall of a scaffold.

FIG. 7 depicts a portion of structural element 141 with a view facing a side wall between the luminal surface and the abluminal surface. An expanded view of a section 148 of structural element 141 is as shown in FIG. 5B. The layers are shown to extend parallel to the cylindrical axis of the scaffold. However, the structural elements can include multilayer regions with layers oriented at any angle relative the cylindrical axis of the scaffold.

In some embodiments, the thickness of the different layers is the same. In other embodiments, the thickness of the different layers can be different. For example, the thickness of the polymer A layer can be greater or smaller than the polymer B layer. In some embodiments, additional extruders may be used to add more different polymers or to ensure that both sides of the scaffold created are of the same polymer so that the entire exposed surface is of the same polymer.

The thickness of the individual layers of the multilayer morphology can be less than 0.01 microns, 0.01 to 0.1 microns, 0.1 to 0.2 microns, 0.2 to 0.5 microns, 1 to 10 microns, 0.5 to 1 micron, 1 to 2 microns, 2 to 3 microns, 3 to 5 microns, or 0.2 to 5 microns. The structural element can include a sufficient number of layers to achieve a desired thickness of the tube and scaffold made from the tube. The thickness of a multilayer tube or multilayer portion of a scaffold may be may be less than 80, 80 to 100 microns, 100 to 120 microns, 120 to 140 microns, 145 to 155 microns, 150 to 155 microns, 140 to 160 microns, 150 to 200 microns, 200 to 250 microns, or greater than 300 microns. Any of the ranges of tube or scaffold thickness may have layer thicknesses in any of the above disclosed layer thickness ranges. The number of layers depends on the multiplying die set up and any additional layers formed after the layer multiplying extrusion process. The tube or scaffold can include 30 to 50 layers, 50 to 100 layers, 100 to 150 layers, 150 to 200 layers, 100 to 200 layers, 200 to 500 layers, 500 to 1000 layers, 1000 to 10,000 layers, or greater than 10,000 layers. The ranges of numbers of layers may correspond to any of the ranges of tube or scaffold thicknesses. All or some of the layers may be from the layer multiplying extrusion process.

The strength, stiffness, and fracture toughness of the scaffold depends on the choice of components, combinations of components for the different layers, their layer thickness, and the interfacial compatibility.

In various embodiments, the multilayer structure includes layers made of a strong, rigid polymer that provides strength and stiffness to the scaffold, which will be referred to as polymer A. These include bioresorbable polymers that are semi-crystalline have a Tg greater than human body temperature or greater than about 37 deg C. The bioresorbable polymers can include aliphatic polyesters. The strong rigid polymer can include copolymers of such semicrystalline polymers. Exemplary polymers include PLLA, poly(D-lactide) (PDLA), polyglycolide (PGA), and poly(L-lactide-co-glycolide) (PLGA). The PLGA can have a mole % of GA between 5 and 50 mol %, or more narrowly, 5-15 mol %. The PLGA can have a mole % of (LA:GA) of 85:15 (or a range of 82:18 to 88:12), 50:50 (or a range of 48:52 to 52:48), 95:5 (or a range of 93:7 to 97:3), or commercially available PLGA products identified being 85:15, 50:50, or 95:5 PLGA.

Polymer A may be characterized by several properties and may have one or any combination of such properties. Polymer A may have an elongation at break less than 20%, 10%, 5%, or 3%. Polymer A may have a modulus of elasticity greater than 3 GPa, 5 GPa, or 7 GPa. Additionally, polymer A may have a Tg greater than body temperature or 37 deg C, or greater than 10 or greater than 20 deg C above human body temperature or 37 deg C. Polymer A may have one or any combination of such properties. The multilayer structure further includes polymer layers made of a polymer with greater a resistance to fracture than polymer A, referred to as polymer B. These polymers can include rubbery polymers or copolymers including rubbery polymers. Such rubbery polymers can include bioresorbable aliphatic polyesters that may have a Tg below human body temperature (or below about 37 deg C) or below ambient temperature, e.g., 25 deg C. The copolymers can include block copolymers with a rubbery block or the rubbery polymer that is a random or alternating copolymer. Examples of biodegradable rubbery polymers include, but are not limited to polyhydroxyalkanoates (PHA), poly(4-hydroxybutyrate) (P4HB), poly(ε-caprolactone) (PCL), poly(trimethylene carbonate) (PTMC), poly(butylene succinate) (PBS), poly(p-dioxanone) (PDO), and poly(ester amides) (PEA). The higher fracture toughness polymer can include a random or block copolymer of PLLA with any of the above rubbery polymers. XY or XYX blocks are also available where block X has a Tg above body temperature and block Y below body temperature. Block X is stiff and block Y is rubbery.

Polymer B may be characterized by several properties and may have one or any combination of such properties. Polymer B may have an elongation at break greater than 30%, 50%, 80%, 100%, 500%, or above 500%. Polymer B may be a flexible material with a modulus of elasticity less than 1.5 GPa, 1 GPa, or 0.5 GPa, or can be 0.5 GPa to 1 GPa at 25 deg C, 37 deg C, or in a range of 25 to 37 deg C. Additionally, polymer B may have a Tg less than body temperature or 37 deg C, less than 25 deg C, or less than 0 deg C.

In further embodiments, the polymer with the greater resistance to fracture, polymer B, can include hydrophilic copolymers of hydrophilic polymers. The copolymer can include block copolymers that have blocks of hydrophilic polymers and blocks of high strength and stiffness polymer, polymer A. The copolymer can include random copolymers of hydrophilic polymers and high strength and stiffness polymers, polymer A. The hydrophilic copolymers can have components that are bioresorbable, water soluble, gel forming, or any combination thereof. Such components may include polyethylene oxide (PEO) or polyethylene glycol (PEG), and polyvinylpyrrolidone (PVP), polyvinyl alcohol (PVA). The higher fracture toughness polymer can include a random or block copolymer of PLLA with any of the above rubbery polymers. Preferred hydrophilic polymers include PEG or an XY or XYX block copolymer containing PEG or PEO where the XY or XYX block copolymer has the following components: X is hydrophobic and Y is hydrophilic. For example, X=PLLA and Y=PEG or PEO. Other preferred polymers or components include hydrophobic ones such as polycaprolactone (PCL). In fact, most of the preferred constructs will be comprised of polymer and copolymers where all components are hydrophobic.

Examples of polymer A can include PLLA-based polymers/copolymers with L-Lactide content between 80 and 100 mol %, or more narrowly, 80 to 85 mol %, 85 to 90 mol %, 90 to 95 mol %, or greater than 95 mol %. These PLLA polymers have a Mn greater than 100 kDa, or more narrowly, 100 to 200 kDa, 200 to 300 kDa, 300 to 400 kDa, or 400 to 500 kDa. The copolymers of the PLLA-based polymers include at least one component including D-lactide, D,L-lactide, glycolide, and caprolactone. These other components listed are examples and no limitation on possibilities is expressed. The copolymers can be random or block copolymers.

Examples of polymer B include lactide/caprolactone copolymers with caprolactone content from 5 to 50 mol %, or more narrowly, 5 to 10 mol %, 10 to 50 mol %, 20 to 50 mol %, 10 to 20 mol %, 20 to 30 mol%, or 30 to 50 mol %. Additional examples of polymer B include lactide/trimethylene carbonate copolymers with trimethylene carbonate content from 5 to 50 mole % or more narrowly, 5 to 10 mol %, 10 to 50 mol %, 20 to 50 mol %, 10 to 20 mol %, 20 to 30 mol %, or 30 to 50 mol %. Preferred copolymers are those with caprolactone or trimethylene carbonate content greater than 10 mol %, but less than or equal to 30 mol %.

Further examples of polymer B can include di-block or tri-block copolymers. The di-block copolymers can be X-Y block copolymers. X can be a hydrophobic bioresorbable polyester block such as PLLA, PGA, or PLGA. The Y block can be a rubbery block such as any of the bioresorbable rubber polyesters including PCL, PTMC, or P4HB. The Y block may also be a hydrophilic polymer such as PEG. The Mn of the X block may be 100 to 300 kDa and the Y block may be 6 to 300 kDa.

The tri-block copolymers can be X-Y-X block copolymers. X can be a hydrophobic bioresorbable polyester block such as PLLA, PGA, or PLGA. The Y block can be a rubbery block such as any of the bioresorbable rubber polyesters including PCL, PTMC, or P4HB. The Y block may also be a hydrophilic polymer such as PEG. The Mn of the X block may be 100 to 300 kDa and the Y block may be 6 to 300 kDa.

In some embodiments, a compatiblizer can be added to the polymers to improve interfacial adhesion between the layers. A "compatibilizer" refers to an interfacial agent that modifies the properties of an immiscible polymer blend or composite which facilitates formation of a uniform blend, and increases interfacial adhesion between the phases. Compatibilization refers to the process of modification of the interfacial properties in an immiscible polymer blend that results in formation of interphases (region of concentration gradient between phases) and stabilization of the morphology. In some embodiments, a compatibilizer can be a block copolymer including blocks that are miscible with the polymer of one layer and blocks that are miscible with the other layer. In one such embodiment, the compatibilizer can include PLLA blocks and PCL for use with alternating layers of PLLA and PCL.

In further embodiments, a nucleating agent can be included in polymer A layers. Generally, in the crystallization of polymers, there are two separate events that occur. The first event is the formation of nuclei in the polymer. The second event is growth of the crystallite around these nuclei. The overall rate of crystallization of the polymer is dependent, therefore, on the equilibrium concentration of nuclei in the polymer, and on the rate of growth of crystallites around these nuclei. Nucleating agents are low molecular weight additives which provide nuclei for heterogeneous crystallization and therefore, increase nucleation density in a polymer. The nucleating agent can include a low molecular weight PDLA at a weight percent of less than 5 wt % of the layer. The PDLA Mn can be less than 100 kDA. This nucleating agent will result in faster crystallization at a lower temperature and smaller crystallites in the layer which enhances fracture toughness.

In addition, the nucleating agent can be selected from the group consisting of magnesium silicate hydrate, ethylene bis (1,2-hydroxystcarylamide), hydroxyapatite, decamethylene-dicarboxylichydrazide, dibenzoylhydrazide, citric acid esters, lactic acid esters, ethyl lactate, triphenyl phosphate, glycerine, and others.

In another embodiment, a polymer layer can include PDLA and PLLA in equal amounts with the PDLA with same or similar Mn as the PLLA to create a stereo-complex. This complex has a melting point in the vicinity of 230° C. and a higher modulus and toughness than PLLA.

In some embodiments, the fabricating process of the scaffold can include intervening processing steps between forming the tubular construct with the multilayer structure and forming the scaffold from the construct. These intervening steps can include a step can induces biaxial orientation through a radial and axial deformation process, annealing the tube, or both.

Prior to laser cutting the tube to form the scaffold, the tube may be radially expanded to increase its radial strength, which also increases the radial strength of the scaffold. The tube can also be axially elongated or extended as well during the expansion process. The radial expansion process tends to preferentially align the polymer chains along the hoop direction which results in enhanced radial strength. The axial elongation similarly increases alignment along the cylindrical axis of the tube. The radial expansion and the axial elongation provide biaxial orientation of the polymer chains which enhances strength and fracture toughness of the material, the tube, and the formed scaffold. The radial expansion step may be crucial to making a scaffold with thin struts, for example less than 150 or 160 microns, that is sufficiently strong to support a lumen upon implantation. The tube with the multilayer structure is radially expanded to a target diameter while heating at a temperature between Tg and the melting point of the polymer. After expansion, the tube is cooled to below the Tg of the polymer, typically to ambient temperature, to maintain the tube at the expanded diameter. The tube is expanded and then cooled at a non-equilibrium rate which then maintains the tube at the expanded diameter. The percent radial expansion may be between 200 and 500%. The percent radial expansion is defined as RE %=(RE ratio −1)×100%, where the RE ratio=(Outside Diameter of Expanded Tube)/(Original Inside Diameter of the tube). The percent of axial extension that the polymer tube undergoes is defined as AE %=(AE ratio −1)×100%, where the AE Ratio=(Length of Extended Tube)/(Original Length of the Tube).

The tube may be radially expanded by blow molding the tube inside of a glass mold. The tube is heated while the pressure in the inside of the tube is increased which expands the tube to the inside diameter of the mold. For example, a heating nozzle blows warm air on the mold as a nozzle translates along length of mold and the tube expands as the nozzle translates. The tube may also be in axial tension resulting in axial elongation.

The temperature of the tube during expansion may be selected to preferentially enhance the fracture resistance of the tube, and hence, the scaffold. The fracture resistance is preferentially enhanced by smaller crystallite domains which are favored at temperatures closer to the Tg of a polymer. For PLLA, the tube may be heated to about 70 to 110° C., or more narrowly, 70 to 95 ° C., during expansion to provide high fracture resistance of a PLLA layer.

When the polymer tube from the extrusion process is radially/axially deformed, the thickness of the tube decreases due to conservation of mass. Therefore, the thickness of the layers of the multilayer morphology decreases when the tube is expanded and axially elongated. Therefore, the thickness of the tube and layers from the layer multiplying extrusion can be adjusted so that the tube thickness and layer thicknesses are at desired values after expansion and elongation.

A scaffold formed from a tube from the layer multiplying process of the present invention without a change in diameter (i.e., not deformation process) will have wall or structural element thickness the same as the tube. In exemplary embodiments, a coronary scaffold may have a wall thickness of about 0.005" to 0.0.008", or more narrowly, 0.0055" to 0.007". The scaffold for SFA applications may have a wall thickness of about 0.008" to 0.014".

A scaffold formed from a deformed tube will have wall or structural element thickness of the deformed tube which will be smaller than the extruded tube. The change in the thickness due to tube deformation depends on the degree of deformation, i.e., radial expansion and axial elongation. The deformed tube thickness is X% of the extruded tube thickness, where X may be 0.1 to 10%, 10 to 20%, 20 to 50%, or 50 to 90% of the extruded tube thickness. In an exemplary embodiment, the extruded tube thickness is at or about 0.02" and the deformed tube thickness is at or about 0.006". The average decrease in thickness of the individual layers of the tube may be equal to the change in thickness of the tube/the number of layers %, however, the change in the layer thickness may not be the same for every layer. The individual thickness layer ranges and number of layer ranges disclosed above apply to extruded tubes, deformed tubes, and scaffolds fabricated there from.

Additionally or alternatively, the tube may be annealed at a temperature between the Tg and the Tm of the polymer of the tube. The annealing can include heating the tube through exposure of the tube to a selected temperature and maintaining the heating for a period of time. The period of time can be 1 to 5 min, 5 min to 1 hr, 1 hr to 3 hr, or 3 to 10 hr. The annealing can be performed without a change in the diameter of the tube. Alternatively, the diameter of the tube may be allowed to change onlydue to the heating. The annealing increases the crystallinity of the tube, which increases the strength of the polymer of the tube. The temperature can be selected to enhance fracture resistance, as discussed above.

The scaffolds of the present invention can be made completely out of the multilayer material. Exemplary stent patterns for coronary applications are described in US 2010/0004735. Other examples of stent patterns are found in US 2008/0275537. The scaffold for coronary applications may have a pre-crimping or as-cut diameter of between 2.5 to 4 mm, or more narrowly, 3 to 3.5 mm.

Polymer scaffolds for coronary artery treatment can have a length between 12 to 36 mm or more narrowly, 12 to 18 mm. The coronary scaffold may be configured for being deployed by a non-compliant or semi-compliant balloon from about a 1.1 to 1.5 mm diameter (e.g., 1.35 mm) crimped profile. Exemplary balloon sizes include 2.5 mm, 3.0 mm, 3.5 mm, and 4.0 mm, where the balloon size refers to a nominal inflated diameter of the balloon. The scaffold may be deployed to a diameter of between 2.5 mm and 5 mm, 2.5 to 4.5 mm, or any value between and including the endpoints. The pressure of the balloon to deploy the scaffold may be 12 to 20 psi. Embodiments of the invention include the scaffold in a crimped diameter over and in contact with a deflated catheter balloon. The intended deployment diameter may correspond to, but is not limited to, the nominal deployment diameter of a catheter balloon which is configured to expand the scaffold. The balloon pressure and the diameter to which the balloon inflates and expands the scaffold may vary from deployment to deployment. For example, the balloon may expand the scaffold in a range between the nominal inflated diameter to the nominal inflated diameter plus 0.5 mm, e.g., a 3.0 mm balloon may expand a scaffold between 3 and 3.5 mm. In any case, the inflated diameter at deployment is less than the rated burst diameter of the balloon.

A scaffold may be laser cut from a tube (i.e., a pre-cut tube) that is less than an intended deployment diameter. In this case, the pre-cut tube diameter may be 0.7 to 1 times the intended deployment diameter or any value or range in between and including the endpoints.

Exemplary stent scaffold patterns for the Superficial Femoral Artery applications are disclosed in US2011/0190872, and US2011/0190871. As compared to coronary stents, a peripheral (SFA) stent scaffold usually has lengths of between about 36 and 40 mm when implanted in the superficial femoral artery, as an example. The scaffold for SFA may have a pre-crimping diameter of between 7 to 10 mm, or more narrowly 7 to 8 mm, and can possess a desired pinching stiffness while retaining at least a 80% recoverability from a 50% crush.

Such scaffolds may further include a polymer coating, which optionally includes a drug. The coating may be conformal (around the perimeter of the scaffold) and may be 1 to 5 microns thick. The scaffolds may be configured for being deployed by a non-compliant balloon. The ratio of deployed to fully crimped diameter can be up to 2.5.

The fabrication methods of a bioabsorbable scaffolds described herein can include the following steps:

(1) forming a polymeric tube using the extrusion process disclosed herein, (2) radially/axially deforming the formed tube, (3) forming a stent scaffolding from the deformed tube by laser machining a stent pattern in the deformed tube with laser cutting, (4) optionally forming a therapeutic coating over the scaffolding, (5) crimping the stent over a delivery balloon, and (6) sterilization with election-beam (E-Beam) radiation.

Detailed discussion of the manufacturing process of a bioabsorbable stent can be found elsewhere, e.g., U.S. Patent Publication No. 20070283552, which is incorporated by reference herein.

Disclosure of ranges includes the endpoints of the stated range.

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. $T_g$ of a given polymer can be dependent on the heating rate and can be influenced by the thermal history of the polymer as well as its degree of crystallinity. Furthermore, the chemical structure of the polymer heavily influences the glass transition by affecting mobility.

The $T_g$ can be determined as the approximate midpoint of a temperature range over which the glass transition takes place. [ASTM D883-90]. The most frequently used definition of $T_g$ uses the energy release on heating in differential scanning calorimetry (DSC). As used herein, the $T_g$ refers to a glass transition temperature as measured by differential scanning calorimetry (DSC) at a 20° C./min heating rate.

The Tg of a polymer, unless otherwise specified, can refer to a polymer that is in a dry state or wet state. The wet state refer to a polymer exposed to blood, water, saline solution, or simulated body fluid. The Tg of the polymer in the wet state can correspond to soaking the polymer until it is saturated.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress—strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a bioresorbable scaffolding including a plurality of structural elements, the structural elements made of a multilayer structure consisting of alternating bioresorbable polymer layers,
   wherein the multilayer structure extends between a luminal layer and an abluminal layer of the bioresorbable polymer layers,
   wherein the layers alternate between a layer of higher strength and stiffness and a layer of greater flexibility wherein a thickness of each of the layers is between about 0.2 and 5 microns and a thickness of the structural elements is between 100 and 200 microns.

2. The stent of claim 1, wherein the multilayer structure includes between 20 and 1000 layers.

3. The stent of claim 1, wherein the multilayer structure comprises alternating layers of a bioresorbable polymer A and a bioresorbable polymer B, wherein the polymer A is an aliphatic polyester with a glass transition temperature (Tg) above 37 deg C and the polymer B is an aliphatic polyester with a Tg below 25 deg C.

4. The stent of claim 1, wherein the multilayer structure comprises alternating layers of a bioresorbable polymer A and a bioresorbable polymer B, wherein the polymer A is a poly(L-lactide) (PLLA) polymer or copolymer with L-lactide content of greater than 80 mol % and the polymer B is a copolymer of PLLA and at least 20 mol % of caprolactone, trimethylene carbonate, or 4-hydroxybutyrate.

5. The stent of claim 1, wherein the multilayer structure comprises alternating layers of a bioresorbable polymer A and a bioresorbable polymer B, wherein the polymer A is a poly(L-lactide) (PLLA) polymer or copolymer with L-lactide content of greater than 80 mol % and the polymer B is a polymer including a hydrophilic polymer component.

6. The stent of claim 1, wherein the multilayer structure comprises alternating layers of a bioresorbable polymer A and a bioresorbable polymer B, wherein the polymer A is a PLLA polymer or copolymer with L-lactide content of greater than 80 mol % and the polymer B is a di-block copolymer of the form X-Y, where the X block is PLLA, polyglycolide (PGA), or poly(L-lactide-co-glycolide) (PLGA) and the Y block is polycaprolactone (PCL), polytrimethylene carbonate (PTMC), poly(4-hydroxybutyrate) (P4HB), or polyethylene glycol (PEG).

7. The stent of claim 1, wherein the multilayer structure comprises alternating layers of a bioresorbable polymer A and a bioresorbable polymer B, wherein the polymer A is a PLLA polymer or copolymer with L-lactide content of greater than 80 mol % and the polymer B is a tri-block copolymer of the form X-Y-X, where the X block is PLLA, PGA, or PLGA and the Y block is PCL, PTMC, P4HB, or PEG.

* * * * *